United States Patent
Becken et al.

(10) Patent No.: US 9,226,657 B2
(45) Date of Patent: Jan. 5, 2016

(54) UNIVERSAL OBJECTIVE REFRACTION

(71) Applicant: Rodenstock GmbH, Munich (DE)

(72) Inventors: Wolfgang Becken, Munich (DE); Helmut Altheimer, Baiswell-Lauchdorf (DE); Gregor Esser, Munich (DE); Andrea Welk, Munich (DE); Matthias Nähring, Munich (DE); Stephan Trumm, Munich (DE)

(73) Assignee: Rodenstock GmbH, Munich (DE)

( * ) Notice: Subject to any disclaimer, the term of this patent is extended or adjusted under 35 U.S.C. 154(b) by 60 days.

(21) Appl. No.: 14/365,260

(22) PCT Filed: Dec. 10, 2012

(86) PCT No.: PCT/EP2012/005092
§ 371 (c)(1),
(2) Date: Jun. 13, 2014

(87) PCT Pub. No.: WO2013/087187
PCT Pub. Date: Jun. 20, 2013

(65) Prior Publication Data
US 2014/0333897 A1 Nov. 13, 2014

(30) Foreign Application Priority Data

Dec. 13, 2011 (DE) .......................... 10 2011 120 973
May 24, 2012 (DE) .......................... 10 2012 010 309

(51) Int. Cl.
*A61B 3/10* (2006.01)
*A61B 3/00* (2006.01)
*A61B 3/103* (2006.01)
*A61B 3/11* (2006.01)
*G02C 7/02* (2006.01)

(52) U.S. Cl.
CPC .............. *A61B 3/103* (2013.01); *A61B 3/0025* (2013.01); *A61B 3/1015* (2013.01); *A61B 3/112* (2013.01); *G02C 7/027* (2013.01); *G02C 7/028* (2013.01)

(58) Field of Classification Search
USPC .................................................. 351/211, 246
See application file for complete search history.

(56) References Cited

U.S. PATENT DOCUMENTS

| 2005/0280777 A1 | 12/2005 | Dai |
| 2009/0006508 A1 | 1/2009 | Youssefi et al. |
| 2011/0149241 A1 | 6/2011 | Dai |

FOREIGN PATENT DOCUMENTS

WO  WO-2005/058136 A2  6/2005

OTHER PUBLICATIONS

Franco, et al. "Real-Time Dynamic Monochromatic Ocular Wavefrong Aberrations During Accommodation: Preliminary Results," IEEE, 2nd Portugese Meeting, 4 pgs., 2012.

*Primary Examiner* — Jack Dinh
(74) *Attorney, Agent, or Firm* — Schiff Hardin LLP

(57) ABSTRACT

The determination of objective refraction data for an eye of a spectacle wearer, wherein based on measured data for the eye of the spectacle wearer, which determine at least one first set of Zernike coefficients of a wave front aberration for a long accommodation and a second set of Zernike coefficients of a wave front aberration for a short accommodation of the eye, objective refraction data for sphere ($Sph_N^{corr}$), cylinder ($Cyl_N^{corr}$) and axis position ($Axis_N^{corr}$) of the eye for close viewing is determined such that the objective refraction data satisfies equations $$Sph_N^{corr} = M_N^{corr} + \sqrt{(J_{N,0}^{corr})^2 + (J_{N,45}^{corr})^2},$$

Figure 1:
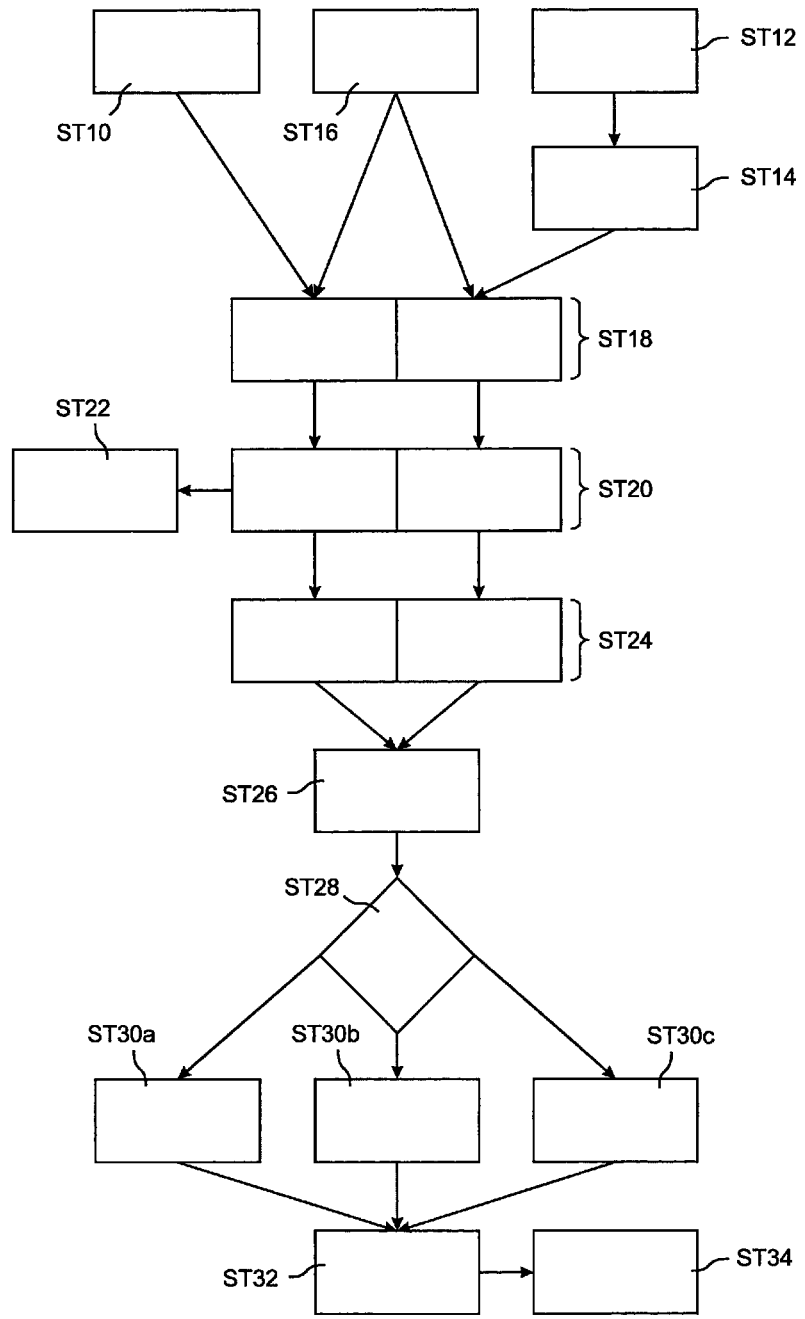

$$Cyl_N^{corr} = -2\sqrt{(J_{N,0}^{corr})^2 + (J_{N,45}^{corr})^2} \text{ and}$$

-continued $$Axis_N^{corr} = \frac{1}{2}\arctan(-J_{N,0}^{corr}, -J_{N,45}^{corr}) + \frac{\pi}{2}$$

for a corrected power vector $P_N^{corr}$ for near viewing, wherein said corrected power vector $P_N^{corr}$ corresponds, based on a difference $$\Delta P = \begin{pmatrix} \Delta M \\ \Delta J \end{pmatrix} = P_N - P_F$$

between a first power vector $$P_F = \begin{pmatrix} M_F \\ J_F \end{pmatrix}$$

and a second power vector $$P_N = \begin{pmatrix} M_N \\ J_N \end{pmatrix}$$

to the value $$P_N - \begin{pmatrix} A_{1N} \\ 0 \\ 0 \end{pmatrix},$$

when $\Delta M > A_{1N}$; and
to the value $$P_F + \frac{A_{1N}}{\Delta M}\begin{pmatrix} 0 \\ \Delta J \end{pmatrix},$$

when $\Delta M \leq A_{1N}$,
wherein $$A_{1N} = -\frac{1}{d}$$

is the spherical equivalent of a predetermined object distance d for close viewing.

26 Claims, 2 Drawing Sheets

UNIVERSAL OBJECTIVE REFRACTION

The present invention relates to an improved objective refraction determination taking into account an objective near refraction. Specifically, in one aspect, the present invention relates to a method, an apparatus, and a computer program product for a fast but yet reliable determination of individual data for at least one eye of a spectacle wearer, which data can be used as flexibly as possible for an individual adaption of a spectacle lens.

For the adaptation of spectacles, spectacle lens producers use increasingly sophisticated methods for individually calculating optical surfaces by considering various individual data of the spectacle wearer particularly with respect to their refraction and the individual situation of wear. On the one hand, this offers a considerable added value for the spectacle wearer due to the improved adaptation of the spectacles or the spectacle lenses to individual needs. On the other hand, however, this added value can only be used fully if the individual data is determined by the optician with sufficient precision in advance. Moreover, since different products of spectacle lens producers often consider different information (e.g. different optical and/or geometric data), it often means a considerable expenditure of time to the optician and accordingly causes trouble to the spectacle wearer each time the required individual data is collected with sufficient precision.

While in a subjective refraction determination the subjective perception of the test person is always considered, objective refraction determinations are performed based on measurements particularly by means of corresponding (preferably automated) measuring apparatuses, specifically without the test person (e.g. spectacle wearer) influencing the measurement course or the measurement values by making statements on their subjective perception.

It is the aim of an objective refraction determination to determine the refraction values required for the correction of a visual defect of a spectacle wearer as reliably as possible.

To this end, for example, usually an autorefractor or an aberrometer is used to determine an objective refraction. Conventionally, these devices determine the refraction for distance vision. Here, the refraction values are either determined directly (autorefractor) or the device internally determines wavefront data including the higher-order aberrations, and therefrom determines a refraction for distance vision. Objective measurements for near vision are not performed here, in particular as the accommodation required for this is difficult to control from a metrological point of view and therefore measurement data is difficult to interpret.

To support in particular the objective refraction determination with the optician, aberrometers are more frequently used. In contrast to conventional eye refractometers, not only the lower-order aberrations (in particular prism, sphere, cylinder, and cylinder axis) are determined, but also the higher-order aberrations (e.g. trefoil, spherical aberration, coma) are detected. Thereby, the measurement also takes account of the fact that some spectacle lens producers also consider these higher-order aberrations in the optimization of some spectacle lens models. In order to be able to use the thus achieved improvement to the optimum extent, exact knowledge of the individual size (and preferably also of the position) of the pupil in the respective situation of wear would be required in turn. As this situation of wear, in turn, would need to be determined individually for the respective spectacle lens model (reading glasses, glasses for drivers, sports glasses), it can already be seen that the sufficiently precise and to-the-individual-situation-adapted determination of user data for the adaptation and optimization of spectacles can involve considerable time and technological effort for the optician and accordingly trouble for the spectacle wearer.

It is the object of the present invention to provide a fast but yet reliable determination of individual data for at least one eye of a spectacle wearer, which data can be used as flexibly as possible for an individual adaption of a spectacle lens. Specifically, it is an object of the present invention to optimize the objective refraction determination such that also near refraction values (near prescription values) can be determined more reliably therewith. This object is in particular solved by a method, an apparatus, and a computer program product with the features according to the independent claims 1, 9, and 10, respectively. Preferred embodiments are subject of the respective subclaims. In a further aspect, this object is in particular solved by a method with the features according to claim 11, an apparatus with the features according to claim 22, and a computer program product with the features according to claim 27. Preferred embodiments are subject of the respective dependent claims.

In one aspect, the invention provides a method for the objective refraction determination for an eye of a spectacle wearer. This method comprises collecting measurement data for the eye of the spectacle wearer, which data specifies at least a first set of Zernike coefficients $c_{2,F}^0$, $c_{2,F}^2$, and $c_{2,F}^{-2}$ for describing a wavefront aberration for a distance accommodation of the eye and a pupil radius $r_0$ relevant to the use of the desired spectacle lens, of the eye, i.e. a pupil radius $r_0$ in a desired situation of wear for the intended spectacle lens, as well as a second set of Zernike coefficients $c_{2,F}^0$, $c_{2,F}^2$, and $c_{2,F}^{-2}$ for describing a wavefront aberration for a near accommodation of the eye and the pupil radius $r_0$ in a situation of wear.

Thus, any of the sets of Zernike coefficients describes aberrations of the eye based on the wavefront aberrations that the eye causes due to refractive errors. They are based on real measurements at the eye of the spectacle wearer, which can be performed e.g. by means of an autorefractor or an aberrometer in a known way. The Zernike coefficients for distance vision, i.e. the coefficients of the first set, can be measured very reliably and reproducibly in a known way, as in particular the distance accommodation of the eye can be controlled or stimulated comparatively well from a metrological point of view. For the measurement for near vision, i.e. for a determination of the second set of Zernike coefficients, preferably a strongest possible accommodation of the eye to near vision is stimulated. Conventionally, it is difficult to assign the degree of near accommodation reliably and reproducibly to a specific object distance or a specific accommodation stimulus. But in the method according to the invention, it is not important to which stimulus or object distance the strongest possible accommodation during the measurement in fact corresponds.

Preferably, the refraction data that can be used directly for optimizing and producing a spectacle lens are determined by means of the invention. In particular, preferably the values for sphere, cylinder, and cylinder axis of the eye for near vision, which apply at an evaluation position for a spectacle lens optimization (e.g. vertex sphere), are determined with a pupil radius actually present in the actual situation of wear of the spectacle lens to be produced. The wavefronts change by propagation and their best approximation through Zernike coefficients depends on the actual pupil radius. Thus, the first and/or second set of Zernike coefficients preferably specifies the Zernike coefficients at the evaluation position and for the pupil radius $r_0$ of the desired situation of wear. Here, it is not necessarily required to measure the wavefront aberrations directly at this position and for the expected brightness.

Instead, the measurement of the wavefront aberrations can also be performed at a different position (e.g. at the corneal vertex) and/or for different lighting conditions. However, if the location of the evaluation position with respect to the measurement position is known, it is also possible to derive the relevant Zernike coefficients at the evaluation position, i.e. they are specified (at least indirectly). Preferred implementations for this will be explained in more detail later on. Correspondingly, the Zernike coefficients for the pupil radius $r_0$ of the desired situation of wear can also be derived from measurements for other (preferably larger) pupil radii as far as e.g. the respective pupil radii are known. Preferred implementations will be presented for this as well at a later point.

The collected measurement data does not need to comprise the first and/or second set of Zernike coefficients directly and thus specify it "directly". Instead, the measurement data can specify the first and/or second set of Zernike coefficients "indirectly" insofar as they can be derived from the collected measurement data. In a method according to the invention, "collecting measurement data" does not need to immediately comprise the process of measuring. Instead, the measurements at the eye of the spectacle wearer can also be performed in advance separately from the present invention (e.g. by an optician or ophthalmologist), and the obtained results can be stored in a user database. For the objective refraction determination according to the invention, the measurement data is collected from this database or from a set of ordered data, for example.

In this description, the pupil radius resulting for the expected lighting conditions in the desired situation of wear will sometimes also be referred to as a photopic pupil radius, without the invention being limited to specific brightnesses of the desired situation of wear in principle. This terminology only is to serve as a delimitation from preferred lighting conditions during a wavefront measurement or aberration measurement of the eye. For example, wavefront measurements are preferably performed with comparatively little light in order to be able to also reliably measure wavefront coefficients (Zernike coefficients) and thus higher-order aberrations due to the large pupil radius resulting here. Therefore, the pupil radius of a measurement situation, which in this case is usually larger, could also be referred to as a mesopic pupil radius in this description—again without limiting the measurement to specific lighting conditions.

According to the invention, only objective refraction data for sphere ($Sph_N^{corr}$), cylinder ($Cyl_N^{corr}$), and cylinder axis ($Axis_N^{corr}$) of the eye for near vision is determined such that the objective refraction data, in dependence on the first and second set of Zernike coefficients, satisfies the equations $$Sph_N^{corr} = M_N^{corr} + \sqrt{(J_{N,0}^{corr})^2 + (J_{N,45}^{corr})^2}$$

$$Cyl_N^{corr} = -2\sqrt{(J_{N,0}^{corr})^2 + (J_{N,45}^{corr})^2}$$

$$Axis_N^{corr} = \frac{1}{2}\arctan(-J_{N,0}^{corr}, -J_{N,45}^{corr}) + \frac{\pi}{2}$$

for a corrected power vector $$P_N^{corr} = \begin{pmatrix} M_N^{corr} \\ J_{N,0}^{corr} \\ J_{N,45}^{corr} \end{pmatrix}$$

for near vision, wherein the corrected power vector $P_N^{corr}$ in dependence on a difference $$\Delta P = \begin{pmatrix} \Delta M \\ \Delta J \end{pmatrix} = P_N - P_F$$

between a first power vector $$P_F = \begin{pmatrix} M_F \\ J_F \end{pmatrix} = \begin{pmatrix} -\frac{4\sqrt{3}}{r_0^2} c_{2,F}^0 \\ -\frac{2\sqrt{6}}{r_0^2} c_{2,F}^2 \\ -\frac{2\sqrt{6}}{r_0^2} c_{2,F}^{-2} \end{pmatrix}$$

and a second power vector $$P_N = \begin{pmatrix} M_N \\ J_N \end{pmatrix} = \begin{pmatrix} -\frac{4\sqrt{3}}{r_0^2} c_{2,N}^0 \\ -\frac{2\sqrt{6}}{r_0^2} c_{2,N}^2 \\ -\frac{2\sqrt{6}}{r_0^2} c_{2,N}^{-2} \end{pmatrix}$$

corresponds to the value $$P_N - \begin{pmatrix} A_{1N} \\ 0 \\ 0 \end{pmatrix},$$

if $\Delta M > A_{1N}$, in particular if $0 \geq \Delta M > A_{1N}$; and corresponds to the value $$P_F + \frac{A_{1N}}{\Delta M}\begin{pmatrix} 0 \\ \Delta J \end{pmatrix},$$

if $\Delta M \leq A_{1N}$, wherein $$A_{1N} = -\frac{1}{d}$$

is the spherical equivalent of a predetermined object distance d for near vision, and wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}$$

Thereby, the present invention overcomes the difficulty in interpreting conventional near measurements. To this end, the invention includes a very reliable and objective possibility of deriving both the distance refraction and the near refraction from a predetermined wavefront measurement for distance vision and a predetermined second wavefront measurement for near vision.

In principle, wavefront measurements by means of e.g. Shack-Hartmann sensors are known. The problem with each wavefront measurement is always the test person's accommodation, due to which an objective measurement (like basically the subjective refraction as well) may turn out to be too myopic. While for distance measurement it has so far been common to achieve, by means of dosed fogging when a target is looked at, that the test person accommodates as little as possible, corresponding procedures for near measurement have been missing until now.

The present invention makes a corresponding fogging for near measurement redundant and yet allows obtaining meaningful near measurement data. To this end, use is particularly made of a distance measurement that provides Zernike coefficients for distance as well as an associated pupil radius. Moreover, use is made of a near measurement that provides Zernike coefficients for near with an associated pupil radius. For near measurement, it is only required for the test person to accommodate, while it is largely irrelevant to which accommodation stimulus this near measurement belongs. Further, it is completely irrelevant how the apparatus makes the patient accommodate. It is of course preferred to use a method that stimulates the patient to accommodate to the maximum extent. To this end, a sequence of near measurements can be performed, the accommodation stimulus of which increases successively, and then the near measurement for which the strongest accommodation took place is selected. Thus, the invention provides a particularly advantageous procedure for obtaining suitable refraction data for a spectacle lens from the given two measurements (distance and near).

Preferably, collecting measurement data for the eye of the spectacle wearer comprises collecting first measurement data for the eye of the spectacle wearer for distance vision, which specifies the first set of Zernike coefficients; collecting a series of second measurement data for the eye of the spectacle wearer for near vision for at least partly different accommodation of the eye; and selecting from the series the measurement data for which the strongest accommodation of the eye occurs as second measurement data, which specifies the second set of Zernike coefficients. In the approach according to the invention, it is not important to which distances the individual accommodation states of near vision belong.

As mentioned, it is not necessary to perform the distance and/or near measurement(s) for the photopic pupil radius $r_0$. Instead, it is rather preferred to perform the measurements of the wavefront aberrations for a larger pupil radius. For example, collecting measurement data for the eye of the spectacle wearer preferably comprises collecting first measurement data for the eye of the spectacle wearer for distance vision, which comprises a first pupil radius $R_F$ (i.e. a pupil radius $R_F$ for a first measurement situation) and a first set of Zernike coefficients for describing a wavefront aberration measured for the first pupil radius $R_F$ and the distance accommodation of the eye. Preferably, in addition to an autorefractor or aberrometer measurement, also the pupil radius $R_F$ during this measurement is measured and optionally stored in a user database as part of the first measurement data.

In addition, collecting measurement data in this embodiment preferably comprises analogously collecting second measurement data for the eye of the spectacle wearer for near vision, which comprises a second pupil radius $R_N$ and a second set of Zernike coefficients for describing a wavefront aberration measured for the second pupil radius $R_N$ and the near accommodation. Here, the lighting conditions and/or the pupil radii $R_F$ and $R_N$ may be the same for the first and second measurement data, i.e. for the distance and near measurements.

Further, preferably independent of the distance and/or near measurement(s) of the aberrations, the photopic pupil radius $r_0$ for the eye of the spectacle wearer (i.e. the pupil radius $r_0$ expected or measured for the situation of wear) is obtained, in particular measured or retrieved from stored individual data. Here, preferably the first and second sets of Zernike coefficients for describing the wavefront aberrations for the photopic pupil radius $r_0$ of the eye are specified by scaling of the first and second sets of Zernike coefficients, respectively, for describing the measured wavefront aberrations depending on the relationship $$\lambda_i = \frac{r_0}{R_i}$$

of the photopic pupil radius $r_0$ to the first (i=F) and second (i=N) pupil radius $R_i$, respectively. Particularly preferably, the sets of Zernike coefficients obtained in or for the measurement situations at least partly comprise Zernike coefficients up to the fourth order (e.g. spherical aberration) or partly even up to the sixth order, wherein "partly" means that not necessarily all Zernike coefficients of the respective order need to be included.

In a preferred embodiment, the first and second sets of Zernike coefficients for describing the measured wavefront aberrations, which are comprised by the first and second measurement data, respectively, comprise at least Zernike coefficients up to the fourth order at least partly, in particular at least the Zernike coefficients of second and fourth orders. Here, the first and second sets of Zernike coefficients for describing the wavefront aberrations for the photopic pupil radius $r_0$ depend on the first (i=F) and second (i=N) sets of Zernike coefficients, respectively, of the measured wavefront aberrations according to $$c_{2,i}^0(r_0) = \lambda_i^2(c_{2,i}^0(R_i) + \sqrt{15}(\lambda_i^2 - 1)c_{4,i}^0(R_i))$$

$$c_{2,i}^2(r_0) = \lambda_i^2(c_{2,i}^2(R_i) + \sqrt{15}(\lambda_i^2 - 1)c_{4,i}^2(R_i))$$

$$c_{2,i}^{-2}(r_0) = \lambda_i^2(c_{2,i}^{-2}(R_i) + \sqrt{15}(\lambda_i^2 - 1)c_{4,i}^{-2}(R_i))$$

The first and second sets of Zernike coefficients ($c_{2,i}^0(r_0)$, $c_{2,i}^2(r_0)$, $c_{2,i}^{-2}(r_0)$) for describing the wavefront aberrations for the photopic pupil radius $r_0$ thus in particular comprise second-order Zernike coefficients and are preferably determined by scaling according to the above context from the second and fourth-order Zernike coefficients ($c_{2,i}^0(R_i)$, $c_{2,i}^2(R_i)$, $c_{2,i}^{-2}(R_i)$, $c_{4,i}^0(R_i)$, $c_{4,i}^2(R_i)$, $c_{4,i}^{-2}(R_i)$) of the measurement data.

In another preferred embodiment, the first and second sets of Zernike coefficients for describing the measured wavefront aberrations, which are comprised by the first and second measurement data, respectively, comprise at least some Zernike coefficients up to the sixth order, in particular at least some of the Zernike coefficients of second, fourth, and sixth orders. Here, the first and second sets of Zernike coefficients for describing the wavefront aberrations for the photopic pupil radius $r_0$ depend on the first (i=F) and second (i=N) sets of Zernike coefficients, respectively, of the measured wavefront aberrations according to $$c_{2,i}^0(r_0) = \lambda_i^2(c_{2,i}^0(R_i) + \sqrt{15}(\lambda_i^2 - 1)c_{4,i}^0(R_i) + \sqrt{21}(\lambda_i^2 - 1)(3\lambda_i^2 - 2)c_{6,i}^0(R_i))$$

$$c_{2,i}{}^2(r_0) = \lambda_i{}^2(c_{2,i}{}^2(R_i) + \sqrt{15}(\lambda_i{}^2-1)c_{4,i}{}^2(R_i) + \sqrt{21}(\lambda_i{}^2-1)(3\lambda_i{}^2-2)c_{6,i}{}^2(R_i))$$

$$c_{2,i}{}^{-2}(r_0) = \lambda_i{}^2(c_{2,i}{}^{-2}(R_i) + \sqrt{15}(\lambda_i{}^2-1)c_{4,i}{}^{-2}(R_i) + \sqrt{21}(\lambda_i{}^2-1)(3\lambda_i{}^2-2)c_{6,i}{}^{-2}(R_i))$$

The first and second sets of Zernike coefficients ($c_{2,i}{}^0(r_0)$, $c_{2,i}{}^2(r_0)$, $c_{2,i}{}^{-2}(r_0)$) for describing the wavefront aberrations for the photopic pupil radius $r_0$ thus in particular comprise second-order Zernike coefficients and are preferably determined by scaling according to the above context from the second, fourth, and sixth-order Zernike coefficients ($c_{2,i}{}^0(R_i)$, $c_{2,i}{}^2(R_i)$, $c_{2,i}{}^{-2}(R_i)$, $c_{4,i}{}^0(R_i)$, $c_{4,i}{}^2(R_i)$, $c_{4,i}{}^{-2}(R_i)$, $c_{6,i}{}^0(R_i)$, $c_{6,i}{}^2(R_i)$, $c_{6,i}{}^{-2}(R_i)$) of the measurement data.

As mentioned, it is not necessary to perform the measurement of the wavefront aberration at the same position as the evaluation. For example, the measurement of the wavefront aberration and its representation by Zernike polynomials could be e.g. in the region of the corneal vertex, while for the optimization and production of a spectacle lens the corresponding wavefront aberrations at the vertex sphere could be considered.

Preferably, collecting measurement data for the eye of the spectacle wearer thus comprises collecting first measurement data for the eye of the spectacle wearer for distance vision, which specifies a first set of Zernike coefficients for describing a wavefront aberration at a first measurement position, which is measured for a distance accommodation of the eye. This set of Zernike coefficients, in turn, can relate either to the photopic pupil radius directly or to a deviating pupil radius, wherein in the latter case scaling may preferably be performed again.

In addition, collecting measurement data for the eye of the spectacle wearer preferably comprises collecting second measurement data for the eye of the spectacle wearer for near vision, which specifies a second set of Zernike coefficients for describing a wavefront aberration at a second measurement position, which is measured for a near accommodation of the eye. Here, the first and second measurement positions may correspond to each other.

Here, determining objective refraction data of the eye for near vision preferably comprises:

determining the first power vector $$P_F(VD_F) = \begin{pmatrix} M_F(VD_F) \\ J_F(VD_F) \end{pmatrix}$$

from the first set of Zernike coefficients, comprised by the first measurement data or scaled depending on $$\lambda_F = \frac{r_0}{R_F}$$

according to a preferred embodiment, depending on a distance $VD_F$ of an evaluation position from the first measurement position such that $M_F(VD_F)$ describes the spherical equivalent and $J_F(VD_F)$ describes the cylindrical portion of the wavefront aberration at the evaluation position for the distance accommodation of the eye; and determining the second power vector $$P_N(VD_N) = \begin{pmatrix} M_N(VD_N) \\ J_N(VD_N) \end{pmatrix}$$

from the second set of Zernike coefficients, comprised by the second measurement data or scaled depending on $$\lambda_N = \frac{r_0}{R_N}$$

according to a preferred embodiment, depending on the distance $VD_N$ of the evaluation position from the second measurement position such that $M_N(VD_N)$ describes the spherical equivalent and $J_N(VD_N)$ describes the cylindrical portion of the wavefront aberration at the evaluation position for the near accommodation of the eye.

The evaluation position may be a position on the spectacle lens (e.g. spectacle lens back surface, position on the vertex sphere), i.e. in particular a position having a distance $VD_i$ from the first and/or second measurement position(s), said distance corresponding to the individual corneal vertex distance of the spectacle wearer for a selected spectacle frame, for example.

In a particularly preferred embodiment, the invention thus provides a method for objective refraction determination for an eye of a spectacle wearer, comprising:

collecting first measurement data for the eye of the spectacle wearer for distance vision, which specifies a first pupil radius $R_F$ and a first set of Zernike coefficients (at least up to the $2^{nd}$ order) for describing a wavefront aberration at a first measurement position, which is measured for the first pupil radius $R_F$ and a distance accommodation of the eye;

collecting second measurement data for the eye of the spectacle wearer for near vision, which specifies a second pupil radius $R_N$ and a second set of Zernike coefficients (at least up to the $2^{nd}$ order) for describing a wavefront aberration at a second measurement position, which is measured for the second pupil radius $R_N$ and a near accommodation;

detecting at least one photopic pupil radius $r_0$ for the eye of the spectacle wearer;

scaling the first and second sets of Zernike coefficients depending on the relationship $$\lambda_i = \frac{r_0}{R_i}$$

of the photopic pupil radius $r_0$ to the first (i=F) and second (i=N) pupil radius $R_i$ for describing first and second scaled wavefront aberrations, respectively, for the eye for the photopic pupil radius at the first and second measurement positions, respectively (this results in the correspondingly scaled set of Zernike coefficients);

determining a first power vector $$P_F(VD_F) = \begin{pmatrix} M_F(VD_F) \\ J_F(VD_F) \end{pmatrix}$$

from the scaled first set of Zernike coefficients depending on the distance $VD_F$ of an evaluation position from the first measurement position such that $M_F(VD_F)$ describes the spherical equivalent and $J_F(VD_F)$ describes the cylindrical portion of the wavefront aberration at the evaluation position for the distance accommodation of the eye;

determining a second power vector $$P_N(VD_N) = \begin{pmatrix} M_N(VD_N) \\ J_N(VD_N) \end{pmatrix}$$

from the scaled second set of Zernike coefficients depending on the distance $VD_N$ of the evaluation position from the second measurement position such that $M_N(VD_N)$ describes the spherical equivalent and $J_N(VD_N)$ describes the cylindrical portion of the wavefront aberration at the evaluation for the near accommodation of the eye;

determining a corrected power vector $P_N^{corr}$ for near vision depending on a difference $$\Delta P = \begin{pmatrix} \Delta M \\ \Delta J \end{pmatrix} = P_N(VD_N) - P_F(VD_F)$$

between the first and second power vectors such that the corrected power vector $P_N^{corr}$
corresponds to the value $$P_N(VD_N) - \begin{pmatrix} A_{1N} \\ 0 \\ 0 \end{pmatrix},$$

if $\Delta M > A_{1N}$, in particular if $0 \geq \Delta M > A_{1N}$; and corresponds to the value $$P_F(VD_F) + \frac{A_{1N}}{\Delta M} \begin{pmatrix} 0 \\ \Delta J \end{pmatrix},$$

if $\Delta M \leq A_{1N}$, wherein $$A_{1N} = -\frac{1}{d}$$

is the spherical equivalent of a predetermined object distance d for near vision; and determining objective refraction data for sphere ($Sph_N^{corr}$), cylinder ($Cyl_N^{corr}$), and cylinder axis ($Axis_N^{corr}$) of the eye for near vision from the corrected power vector $P_N^{corr}$.

In particular, the refraction data for sphere ($Sph_N^{corr}$), cylinder ($Cyl_N^{corr}$), and cylinder axis ($Axis_N^{corr}$) of the eye for near vision according to $$Sph_N^{corr} = M_N^{corr} + \sqrt{(J_{N,0}^{corr})^2 + (J_{N,45}^{corr})^2}$$

$$Cyl_N^{corr} = -2\sqrt{(J_{N,0}^{corr})^2 + (J_{N,45}^{corr})^2}$$

$$Axis_N^{corr} = \frac{1}{2}\arctan(-J_{N,0}^{corr}, -J_{N,45}^{corr}) + \frac{\pi}{2}$$

is determined from the corrected power vector $P_N^{corr}$.

Preferably, the first power vector and/or the second power vector is determined such that it satisfies the equation $$P_i(VD_i) = \begin{pmatrix} Sph_i(VD_i) + \frac{Cyl_i(VD_i)}{2} \\ -\frac{Cyl_i(VD_i)}{2}\cos 2Axis_i(VD_i) \\ -\frac{Cyl_i^2(VD_i)}{2}\sin 2Axis_i(VD_i) \end{pmatrix}$$

with $$Sph_i(VD_i) = \frac{Sph_i(0)}{1 + VD_i \times Sph_i(0)}$$

$$Cyl_i(VD_i) = \frac{Sph_i(0) + Cyl_i(0)}{1 + VD_i \times (Sph_i(0) + Cyl_i(0))} - \frac{Sph_i(0)}{1 + VD_i \times Sph_i(0)}$$

$$Axis_i(VD_i) = Axis_i(0)$$

and $$Sph_i(0) = -\frac{4\sqrt{3}}{r_0^2}c_{2,i}^0 + \frac{2\sqrt{6}}{r_0^2}\sqrt{(c_{2,i}^{-2})^2 + (c_{2,i}^2)^2}$$

$$Cyl_i(0) = -\frac{4\sqrt{6}}{r_0^2}\sqrt{(c_{2,i}^{-2})^2 + (c_{2,i}^2)^2}$$

$$Axis_i(0) = \frac{1}{2}\arctan(c_{2,i}^2, c_{2,i}^{-2}) + \frac{\pi}{2}$$

for i=F, N, wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}$$

and wherein $c_{2,i}^0$, $c_{2,i}^2$, and $c_{2,i}^{-2}$ designate the second-order Zernike coefficients for distance vision (i=F) and near vision (i=N), which are comprised by the first (i=F) and (i=N) measurement data, respectively, or scaled according to a preferred embodiment.

In a preferred embodiment, collecting the first and/or or second measurement data comprises measuring refraction data and/or wavefront aberrations of the eye by means of an autorefractor and/or by means of an aberrometer.

Preferably, the invention provides a method for optimizing and producing a spectacle lens for at least one eye of a spectacle wearer, comprising:

an inventive method for objective refraction determination for the at least one eye of the spectacle wearer particularly according to one of the preferred embodiments described herein;

optimizing or calculating a spectacle lens for correcting the objectively determined refraction; and producing the spectacle lens according to the result of the optimization or calculation.

In another aspect, the invention provides an apparatus for objective refraction determination for an eye of a spectacle wearer, comprising:

a measurement data collecting interface for collecting measurement data for the $c_{2,F}^0$, $c_{2,F}^2$, and $c_{2,F}^{-2}$ for describing a wavefront aberration for a distance accommodation and a photopic pupil radius $r_0$ of the eye, and a second set of Zernike coefficients $c_{2,N}^0$, $c_{2,N}^2$, and $c_{2,N}^{-2}$ for describing a wavefront aberration for a near accommodation and the photopic pupil radius $r_0$ of the eye; and a refraction data determining device for determining objective refraction data for sphere ($Sph_N^{corr}$), cylinder ($Cyl_N^{corr}$), and cylinder axis ($Axis_N^{corr}$) of the eye for near vision such that the objective refraction data, in dependence on the first and second sets of Zernike coefficients, satisfies the equations $$Sph_N^{corr} = M_N^{corr} + \sqrt{(J_{N,0}^{corr})^2 + (J_{N,45}^{corr})^2}$$
$$Cyl_N^{corr} = -2\sqrt{(J_{N,0}^{corr})^2 + (J_{N,45}^{corr})^2}$$
$$Axis_N^{corr} = \frac{1}{2}\arctan(-J_{N,0}^{corr}, -J_{N,45}^{corr}) + \frac{\pi}{2}$$

for a corrected power vector $$P_N^{corr} = \begin{pmatrix} M_N^{corr} \\ J_{N,0}^{corr} \\ J_{N,45}^{corr} \end{pmatrix}$$

for near vision, wherein the corrected power vector $P_N^{corr}$, in dependence on a difference $$\Delta P = \begin{pmatrix} \Delta M \\ \Delta J \end{pmatrix} = P_N - P_F$$

between a first power vector $$P_F = \begin{pmatrix} M_F \\ J_F \end{pmatrix} = \begin{pmatrix} -\frac{4\sqrt{3}}{r_0^2} c_{2,F}^0 \\ -\frac{2\sqrt{6}}{r_0^2} c_{2,F}^2 \\ -\frac{2\sqrt{6}}{r_0^2} c_{2,F}^{-2} \end{pmatrix}$$

and a second power vector $$P_N = \begin{pmatrix} M_N \\ J_N \end{pmatrix} = \begin{pmatrix} -\frac{4\sqrt{3}}{r_0^2} c_{2,N}^0 \\ -\frac{2\sqrt{6}}{r_0^2} c_{2,N}^2 \\ -\frac{2\sqrt{6}}{r_0^2} c_{2,N}^{-2} \end{pmatrix}$$

corresponds to the value $$P_N - \begin{pmatrix} A_{1N} \\ 0 \\ 0 \end{pmatrix},$$

if $\Delta M > A_{1N}$, in particular if $0 \geq \Delta M > A_{1N}$; and
corresponds to the value $$P_F + \frac{A_{1N}}{\Delta M}\begin{pmatrix} 0 \\ \Delta J \end{pmatrix},$$

if $\Delta M \leq A_{1N}$, wherein $$A_{1N} = -\frac{1}{d}$$

is the spherical equivalent of a predetermined object distance d for near vision, and wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}$$

Preferably, the apparatus comprises calculating means adapted to determine or calculate the refraction data according to a method for refraction determination according to the present invention in particular in a preferred embodiment.

In a further aspect, which can preferably be used together with the above-described aspects or alone, the invention provides a method for collecting a set of individual user data for the adaptation and optimization of spectacles, comprising the following steps: First of all, the method comprises a step of collecting first aberrometric data of a first eye of the spectacle wearer for a first accommodation state of the first eye for a first primary brightness. Particularly preferably, a distance accommodation is provided as the first accommodation state. As the first primary brightness, preferably a brightness in the regime of mesopic vision (preferred luminance in the range from approximately 0.003 cdm² to approximately 30 cdm², particularly preferably in the range from approximately 0.003 cdm² to approximately 3 cdm², even more preferably in the range from approximately 0.003 cdm² to approximately 0.3 cdm², most preferably in the range from approximately 0.003 cdm² to approximately 0.03 cdm²) is provided. Here, brightness is particularly always understood to be the brightness at the location of the eye or that is to be captured by the eye.

In the context of this description, "aberrometric data" (or "aberrometric measurements") is understood to be data for describing the aberrations of an eye (measurements for obtaining this data), the information content of which corresponds at least to the term of the order "defocus" in the case of illustration with Zernike coefficients, but in the ideal case includes higher orders (e.g. cylinder error, coma, and spherical aberration).

After the step of collecting first aberrometric data of the first eye, the method preferably comprises a step of collecting second aberrometric data of the first eye of the spectacle wearer for a second accommodation state of the first eye for a second primary brightness. Here, the second primary brightness preferably corresponds to the first primary brightness. As the second primary brightness, preferably also a brightness in the regime of mesopic vision (preferred luminance in the range from approximately 0.003 cdm² to approximately 30 cdm², particularly preferably in the range from approximately 0.003 cdm² to approximately 3 cdm², even more preferably in the range from approximately 0.003 cdm² to approximately 0.3 cdm², most preferably in the range from approximately 0.003 cdm² to approximately 0.03 cdm²) is provided. Particularly preferably, a near accommodation is provided as the second accommodation state.

Together with collecting first aberrometric data and/or collecting second aberrometric data (i.e. for the first and second primary brightnesses and for the first and second accommodation states, respectively), first and second primary pupillometric data, respectively, for the first eye is collected. The term "pupillometric data" (or pupillometric measurements) refers to information on the size of the pupil (or measurements for obtaining this data), which comprise at least one size specification (e.g. in the form of a radius), but can also represent the shape of the pupil in a complex form. In addition, the pupillometric data can include information on the position of the pupil (e.g. relative to the corneal vertex or to the optical axis of the eye).

Particularly preferably, together with collecting first aberrometric data and second aberrometric data, first primary pupillometric data for the first accommodation state and second primary pupillometric data for the second accommodation state are collected, respectively.

After collecting the first and preferably second aberrometric data (and thus also after collecting primary pupillometric data, in particular the first and second primary pupillometric data), the method further comprises a step of collecting secondary pupillometric data for the first eye of the spectacle wearer for a secondary brightness, the value of which being above that of the first (and preferably second) primary brightness. As the secondary brightness, preferably a brightness in the regime of photopic vision (preferred luminance in the range from approximately 3 cdm² to approximately 30 cdm²) is provided.

In this description, the designations "primary" and "secondary" for the brightnesses and the pupillometric data merely serve for a better understanding of the assignment of the individual variables in the course of the method and are of no further technical significance. For example, for a better understanding of the description, the variables specified or acquired together with the aberrometric data are given the additional designation "primary", while the variables set or acquired after or according to the aberrometric data or measurements are referred to as "secondary".

Here, the brightnesses used for collecting the pupillometric data can either be adapted at least partly to the conditions corresponding to the individual situation of wear or be specified independent thereof. In the latter case—if desired—the values of the individual data, which correspond to an individual situation of wear, can be determined very easily e.g. by interpolation and/or extrapolation in particular on the basis of an adapted analytical function.

Thus, the invention provides a very efficient possibility of determining a universal objective refraction with minimum effort for the user (e.g. optician) and the test person (e.g. customer). The term universal objective refraction refers to an objective refraction which comprises the aberrometric values of the entire eye (e.g. the imaging of objects on the retina) for at least one, preferably two accommodation states (e.g. distance and near) as well as pupillometric data for at least two lighting states (e.g. photopic and mesopic), from which a plurality of different situations of wear can be arrived very easily but yet reliably.

After the step of collecting first aberrometric data of the first eye, optionally after the step of collecting second aberrometric data of the first eye, and prior to the step of collecting secondary pupillometric data of the first eye, the method preferably comprises the following steps in this order:

collecting first aberrometric data of a second eye of the spectacle wearer for a first accommodation data of the second eye for the first primary brightness; and collecting second aberrometric data of the second eye of the spectacle wearer for a second accommodation state of the second eye for the second primary brightness.

Analogous to the first eye, a distance accommodation and a near accommodation are provided as a first accommodation state of the second eye and as a second accommodation state of the second eye, respectively. Also analogous to the first eye, in this preferred embodiment, first and second primary pupillometric data for the second eye is collected together with collecting first aberrometric data and/or second aberrometric data of the second eye (i.e. for the first and second primary brightnesses, respectively). After collecting the first and second aberrometric data of the second eye and prior to collecting secondary pupillometric data of the first eye, the method further comprises a step of collecting secondary pupillometric data of the second eye of the spectacle wearer for the secondary brightness.

Preferably, the first accommodation state of the first and/or second eye(s) corresponds to a distance accommodation, and the second accommodation state of the first and/or second eye(s) corresponds to a near accommodation. Preferably, the accommodation states of the first and/or second eye(s) are stimulated by projecting a virtual target into the respective eye. Particularly preferably, between collecting the first and second aberrometric data of the first and/or second eye(s), the method comprises a step of continuously approximating a virtual position of the virtual target to the first or second eye. Thereby, the correct accommodation of the eye to the virtual target is caused in a particularly reliable manner, which results in a particularly reliable measurement of the aberrometric data and optionally of the pupillometric data for the lower brightness (also referred to as primary pupillometric data here).

Preferably, the method further comprises collecting further (third or even fourth, etc.) aberrometric data of the first and/or second eye(s) of the spectacle wearer for a third (or fourth, etc.) accommodation state of the first or second eye for a third (or fourth, etc.) primary brightness, wherein preferably third (or fourth, etc.) primary pupillometric data for the first or second eye is collected together with collecting third (or fourth, etc.) aberrometric data of the first or second eye. Preferably, this takes place after collecting the first aberrometric data of the first or second eye. Particularly preferably, the second, third, fourth, etc. accommodation correspond to different near accommodations. In a further preferred aspect, all primary brightnesses are the same.

In a further preferred embodiment, together with collecting the secondary pupillometric data of the first and/or second eye(s), topographic data of the first or second eye for the secondary brightness is collected. "Topographic data" (or "topographic measurements") is understood to be data for describing the topography of a cornea (or measurements for acquiring this data), the information content of which corresponds at least to the term of the order "defocus" in the case of illustration with Zernike coefficients, but in the ideal case includes higher orders (e.g. cylinder error, coma, and spherical aberration).

Since the topographic data is collected together with the pupillometric data for the high brightness (in particular also referred to as secondary pupillometric data here), no additional measurement time and no additional adjustment of the respective eye are required. The additional topographic data is also available for an improved optimization of a spectacle lens, without the optician having any noticeable additional effort. As will be explained later on, a pattern projector used for the topographic measurement can also provide for the secondary brightness at which the pupillometric data of the higher brightness (in particular photopic pupillometric data) is collected.

Preferably, collecting topographic data comprises projecting a light pattern onto the eye and collecting image data of the eye by means of a single image-capturing device (camera), from which both the light reflections, generated by the projected light pattern, for evaluating the topographic data and the pupillometric data is determined. In a preferred embodiment, the image-capturing device comprises a color camera, wherein the projected light pattern can be distinguished from the pupil comprised in the image data in terms of color. Thereby, an easier evaluation of the pupillometric data and the topographic data from the same image date set can be attained. Alternatively, two different cameras having different color filters, for example, may be provided for collecting the topographic data and the pupillometric data in order to also achieve an easier evaluation of the respective image elements.

In a further aspect, which can preferably be used together with the above-described aspects or alone, the invention provides an apparatus for collecting a set of individual user data for adapting and optimizing spectacles, the apparatus comprising:
  an aberrometer device for collecting aberrometric data of at least one eye of the spectacle wearer at least for a first accommodation state of the eye for a first primary brightness and preferably for a second accommodation state of the eye for a second primary brightness;
  an illuminating device for generating a secondary brightness greater than the first (and preferably second) primary brightness; and
  a pupillometer device adapted to collect first primary pupillometric data of the at least one eye for the first primary brightness and/or second primary pupillometric data of the at least one eye for the second primary brightness, and to collect secondary pupillometric data of the at least one eye for the secondary brightness,
  wherein the apparatus is adapted to perform a method according to the present invention, in particular in one of the embodiments described herein.

Preferably, the aberrometer device comprises an accommodation stimulation device adapted to project a virtual target into the at least one eye and to change the virtual position of the virtual target between a position for stimulating a distance accommodation and a position for stimulating a near accommodation. As a virtual target one considers particularly an optical projection into the eye of the test person such that this projection creates an image on the cornea of the eye, which image corresponds to the image of a real object at a specific distance from the eye. This specific distance is also referred to as the virtual position for the virtual target here. Since in particular it is not a real object, also a virtual position beyond infinity can be simulated for projection by a suitable construction of the optical system.

The apparatus preferably comprises:
  a pattern projector for projecting a light pattern onto the at least one eye (in particular onto the cornea of the at least one eye); and
  a topography evaluation device adapted to determine topographic data from reflections of the light pattern at the eye (in particular at the cornea of the eye).

In a preferred embodiment, the pattern projector also serves as the above-described illuminating device for generating the secondary brightness.

In addition to corresponding methods particularly for refraction determination preferably using one or more of the corresponding method steps implemented as functional procedures in the apparatuses according to the invention, the invention provides a computer program product, in particular in form of a storage medium or a sequence of signals, comprising computer-readable instructions, which, when loaded in a storage of a computer, preferably in the storage of a data-processing unit of an apparatus according to the present invention, in particular in one of the preferred embodiments described herein, and executed on the computer, which in particular is adapted to control an apparatus according to the invention or is comprised an apparatus according to the invention, cause the computer (and thus in particular the apparatus according to the invention) to perform or control a method according to the present invention, in particular according to a preferred embodiment thereof.

The invention will be described based on preferred embodiments by way of example in the following with reference to the accompanying drawings, which show:

FIG. 1 a flow chart for schematically illustrating a method process according to the preferred embodiment of the invention.

Figure 2:
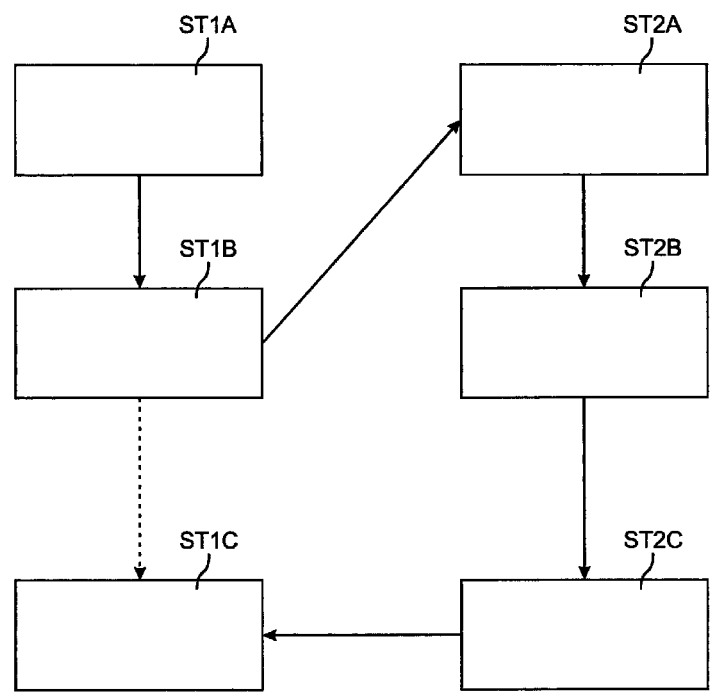

FIG. 2 a schematic illustration of a process of a method according to a preferred embodiment of the present invention.

In a preferred embodiment, the Zernike coefficients for distance vision and near vision are retrieved from a data set provided for the spectacle wearer. This data set may have been generated in separate measurements and been stored for further use and evaluation or for a prescription of spectacles. For example, an optician may generate the data set by measurement of wavefronts at the eye of the spectacle wearer and communicate it to a spectacles manufacturer or an optical computing office for further processing, in particular for further use for a method according to the invention. It is also possible that the optician disposes of a corresponding computer system, which determines corrected near refraction data, in the way according to the invention, on the basis of the data set possibly determined possibly in a separate measurement for the spectacle wearer, which corrected near refraction data can subsequently be transferred to a spectacle manufacturer, for example. On the other hand, it is also possible to further process near and/or distance refraction data or Zernike coefficients for near and distance vision after the measurement directly in a manner according to the invention for (objective) refraction determination, in particular without being stored in a user database beforehand.

Irrespective of how the measurement values or measurement data for a refraction determination according to the invention are detected, the preferred embodiment illustrated in FIG. 1 comprises a step ST10 of collecting first measurement data that may be based in particular on a conventional objective refraction determination for distance vision, i.e. for the least possible accommodation of the eye. In a preferred embodiment, the measurement data comprises a plurality of Zernike coefficients measured under mesopic conditions and a resulting pupil radius $R_0$. Therefore, the first measurement data comprises in particular the pupil radius, which is or was measured preferably also during the objective refraction determination, as well as a set of Zernike coefficients $c_{n,F}^m$ ($R_0$) (first set of Zernike coefficients), which describe the wavefront aberration e.g. at the corneal vertex for a distance accommodation of the eye.

Analogously, in a step ST12, measurement data for a near accommodation of the eye is collected or measured. To this end, a sequence (series) of near measurements can be performed, the accommodation stimulus of which increases successively. Subsequently, in step ST14, the near measurement for which the strongest accommodation took place is selected, i.e. where ΔM shows the most negative value, as will be described in equation (9b) later on. Thus, the measurement data collected in steps ST12 and ST14 preferably comprise the pupil radius $R_0$ during the measurement and a set of Zernike coefficients $c_{n,\mathcal{N}}{}^m(R_0)$ (second set of Zernike coefficients), which describe the wavefront aberration e.g. at the corneal vertex for a near accommodation of the eye. It is not important which accommodation stimulus or object distance has led to the maximum accommodation.

Where the following observations can be applied to distance and near accommodations analogously, the corresponding index ("F" for distance and "N" for near) can be omitted in the formulae.

If the Zernike coefficients for a (mesopic) pupil radius $R_0$, included in the collected measurement data, are given as $c_n{}^m(R_0)$, then the concentric section of the same wavefront has Zernike coefficients $c_n{}^m(r_0)$ for a (photopic) pupil radius $r_0 < R_0$, which can be derived from $c_n{}^m(R_0)$ and the radii ratio $\lambda = r_0/R_0$ preferably by means of the scaling relation $$c_2{}^0(r_0) = \lambda^2(c_2{}^0(R_0) + \sqrt{15}(\lambda^2-1)c_4{}^0(R_0) + \sqrt{21}(\lambda^2-1)(3\lambda^2-2)c_6{}^0(R_0))$$

$$c_2{}^2(r_0) = \lambda^2(c_2{}^2(R_0) + \sqrt{15}(\lambda^2-1)c_4{}^2(R_0) + \sqrt{21}(\lambda^2-1)(3\lambda^2-2)c_6{}^2(R_0))$$

$$c_2{}^{-2}(r_0) = \lambda^2(c_2{}^{-2}(R_0) + \sqrt{15}(\lambda^{-2}-1)c_4{}^{-2}(R_0) + \sqrt{21}(\lambda^2-1)(3\lambda^2-2)c_6{}^{-2}(R_0)) \quad (0)$$

To this end, the method preferably comprises a step ST16 of detecting or measuring a preferably individual photopic pupil radius $r_0$. Preferably, in a step ST18 of scaling the Zernike coefficients both for distance vision and for near vision, the relation according to equation (0) is used to scale down a measurement pertaining to a (large) mesopic pupil to a (smaller) photopic reference pupil.

For a further description, preferably power vectors $$P = \begin{pmatrix} M \\ J_0 \\ J_{45} \end{pmatrix} \quad (1)$$

are used. For a later simplification, the cylindrical portion of P is summarized as $$J = \begin{pmatrix} J_0 \\ J_{45} \end{pmatrix} \quad (1a)$$

so that the power vector can also be written in the form $$P = \begin{pmatrix} M \\ J \end{pmatrix} \quad (1b)$$

To establish a connection between Zernike coefficients and SCA values (refraction data for sphere, cylinder, axis) to be valid in the same reference plane (i.e. the same evaluation position), preferably the following formulae are applied, according to which the power vector $$P(Sph, Cyl, Axis) = \begin{pmatrix} Sph + \dfrac{Cyl}{2} \\ -\dfrac{Cyl}{2}\cos 2 Axis \\ -\dfrac{Cyl}{2}\sin 2 Axis \end{pmatrix} \quad (2)$$

$$P(c_2^0, c_2^{-2}, c_2^2) = \begin{pmatrix} -\dfrac{4\sqrt{3}}{r_0^2}c_2^0 \\ -\dfrac{2\sqrt{6}}{r_0^2}c_2^2 \\ -\dfrac{2\sqrt{6}}{r_0^2}c_2^{-2} \end{pmatrix}$$

can either be considered a function of the refraction data Sph, Cyl, Axis or a function of the Zernike coefficients $c_2{}^0, c_2{}^2, c_2{}^{-2}$, wherein $r_0$ is the pupil radius. In this respect, reference is also made to page 334 in "Adaptive Optics for Vision Science", Porter et al., Wiley 2006. This results in $$Sph = -\dfrac{4\sqrt{3}}{r_0^2}c_2^0 + \dfrac{2\sqrt{6}}{r_0^2}\sqrt{(c_2^{-2})^2 + (c_2^2)^2} \quad (3a)$$

$$Cyl = -\dfrac{4\sqrt{6}}{r_0^2}\sqrt{(c_2^{-2})^2 + (c_2^2)^2}$$

$$Axis = \dfrac{1}{2}\arctan(c_2^2, c_2^{-2}) + \dfrac{\pi}{2}$$

$$Sph = M + \sqrt{J_0^2 + J_{45}^2} \quad (3b)$$

$$Cyl = -2\sqrt{J_0^2 + J_{45}^2}$$

$$Axis = \dfrac{1}{2}\arctan(-J_0, -J_{45}) + \dfrac{\pi}{2}$$

wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}$$

The equations (3a) and (3b) are equivalent to equations (2) and yield Sph, Cyl, Axis for given Zernike coefficients in the same reference plane and given pupil radius.

If the measurement position(s) (e.g. the plane of the corneal vertex) differ(s) from the plane or evaluation position of interest (e.g. the spectacle lens plane or the vertex sphere) and is distant therefrom by a corneal vertex distance VD, then the propagated refraction data is preferably determined by $$Sph(VD) = \dfrac{Sph(0)}{1 + VD \times Sph(0)} \quad (4)$$

$$Cyl(VD) = \dfrac{Sph(0) + Cyl(0)}{1 + VD \times (Sph(0) + Cyl(0))} - \dfrac{Sph(0)}{1 + VD \times Sph(0)}$$

$$Axis(VD) = Axis(0)$$

Correspondingly, the method preferably comprises a step ST20 of determining or calculating propagated refraction values, i.e. the refraction values for sphere, cylinder, and cylinder axis of propagated wavefront, from the refraction values at the measurement positions, which are particularly determined from the original or scaled Zernike coefficients according to equation (3a).

To determine the objective refraction, the entire method preferably provides objective refraction values both for distance vision and for near vision. Here, the steps ST18 of scaling the Zernike coefficients and ST20 of determining propagated refraction values are performed both for the first measurement data (distance vision) and for the second measurement data (near vision).

Preferably, the measured Zernike coefficients of the distance measurement, which can be given by $(c_{2,F}^0(R_{0,F}), c_{2,F}^2(R_{0,F}), c_{2,F}^{-2}(R_{0,F}))$ in the $2^{nd}$ order, are scaled down in step ST18 to the values $(c_{2,F}^0(r_0), c_{2,F}^2(r_0), c_{2,F}^{-2}(r_0))$ for the photopic pupil radius by means of equation (0) with $\lambda = r_0/R_{0,F}$. Here, $R_{0,F}$ is the measured mesopic pupil radius, which belongs to the data of the distance measurement, while $r_0$ is the photopic pupil radius, which may originate from a separate measurement ST16.

The scaled Zernike coefficients resulting in step ST18 are then transformed to refraction data $Sph_F(0), Cyl_F(0), Axis_F(0)$ for distance by means of equation (3a), wherein in equation (3a) the Zernike coefficients $c_2^0, c_2^2, c_2^{-2}$ are replaced by the photopic Zernike coefficients $c_{2,F}^0(r_0), c_{2,F}^2(r_0), c_{2,F}^{-2}(r_0)$ for distance, which are preferably determined according to equation (0).

The distance refraction data $Sph_F(0), Cyl_F(0), Axis_F(0)$ is transformed in step ST20 preferably by means of equation (4) to obtain the refraction data $Sph_F(VD), Cyl_F(VD), Axis_F(VD)$ valid at the evaluation position at the distance VD from the measurement position. In step ST22, the propagated distance refraction data $Sph_F(VD), Cyl_F(VD), Axis_F(VD)$ is output as objective refraction values for distance vision.

For the determination of the near refraction values, the method according to the invention comprises, in particular in the preferred embodiment illustrated in FIG. 1, initially analogous steps as for the distance refraction values. Since the data of the distance measurement is also relevant for the interpretation of the near measurement, both near and distance refraction data is determined from the existing Zernike coefficients. With regard to the distance refraction, the results $Sph_F(VD), Cyl_F(VD), Axis_F(VD)$ can be used as described above. For the near measurement, preferably analogous steps are performed initially.

Preferably, the measured Zernike coefficients of the near measurement, which may be given by $c_{2,N}^0(R_{0,N}), c_{2,N}^2(R_{0,N}), c_{2,N}^{-2}(R_{0,N})$ in the $2^{nd}$ order, are scaled down in step ST18 to the values $c_{2,N}^0(r_0), c_{2,N}^2(r_0), c_{2,N}^{-2}(r_0)$ for the photopic pupil radius by means of equation (0) with $\lambda = r_0/R_{0,N}$. Here, $R_{0,N}$ is the measured mesopic pupil radius, which belongs to the data of the near measurement, while $r_0$ is the photopic pupil radius, which may originate from a separate measurement ST16.

The scaled Zernike coefficients resulting in step ST18 are then transformed to refraction data $Sph_N(0), Cyl_N(0), Axis_N(0)$ for near by means of equation (3a), wherein in equation (3a) the Zernike coefficients $c_2^0, c_2^2, c_2^{-2}$ are replaced by the photopic Zernike coefficients $c_{2,N}^0(r_0), c_{2,N}^2(r_0), c_{2,N}^{-2}(r_0)$ for near, which are preferably determined according to equation (0).

The near refraction data $Sph_N(0), Cyl_N(0), Axis_N(0)$ is transformed in step ST20 preferably by means of equation (4) to obtain the refraction data $Sph_N(VD), Cyl_N(VD), Axis_N(VD)$ valid at the evaluation position at the distance VD from the measurement position.

In a following step ST24, preferably the propagated distance refraction data $Sph_F(VD), Cyl_F(VD), Axis_F(VD)$ is transformed to power vectors by means of equation (2), i.e.

$$P_F(VD) = P(Sph_F(VD), Cyl_F(VD), Axis_F(VD)) \tag{8a}$$

and analogously, the power vector belonging to the propagated near refraction data $Sph_N(VD), Cyl_N(VD), Axis_N(VD)$ is formed by $$P_N(VD) = P(Sph_N(VD), Cyl_N(VD), Axis_N(VD)) \tag{8b}$$

Now, to interpret the near measurement data, the difference between distance measurement data and near measurement data, i.e. the difference power vector $$\Delta P = P_N(VD) - P_F(VD) \tag{9a}$$

is formed in the power vector space in step ST26. Written separately in spherical and cylindrical components, this correspond to $$\Delta M = M_N(VD) - M_F(VD)$$

$$\Delta J = J_N(VD) - J_F(VD) \tag{9b}$$

The power vector in equation (8b) primarily describes the properties of the wavefront during the measurement. To obtain refraction data that is crucial as the correction for a spectacle lens from this, it is not taken into consideration that the spectacle lens in the near zone is not intended to support distance vision, but near vision, preferably at an object distance of preferably $A_{1N} = 2.5$ dpt, which corresponds to an object distance of 40 cm. With regard to equation (8b), the power vector is corrected by values that depend on the object distance. To form a corrected power vector $P_N^{corr}(VD)$ of the near measurement, preferably three cases are distinguished in step ST28 of comparing the spherical component of the difference power vector:

a) M>0

In this case, the accommodation during the near measurement is even lower than during the distance measurement. This suggests, for example, that either at least one of the two measurements is not reliable, or that the noise in the measurement data has caused the case $\Delta M > 0$. In a preferred embodiment, in the case $\Delta M > 0$, one of the two measurements is discarded and replaced by the other one in step ST30*a*. Particularly preferably, in this case the original near measurement is replaced by $$P_N^{corr}(VD) = P_F(VD) - \begin{pmatrix} A_{1N} \\ 0 \\ 0 \end{pmatrix} \tag{10}$$

In another preferred embodiment, the two measurements are interchanged in step ST30*a*. In this embodiment, the corrected power vectors are thus determined by:

$$P_F^{corr}(VD) = P_N(VD) \tag{10a}$$

$$P_N^{corr}(VD) = P_F(VD) - \begin{pmatrix} A_{1N} \\ 0 \\ 0 \end{pmatrix}$$

b) $A_{1N} < \Delta M \leq 0$, wherein preferably $A_{1N} = -2.5$ dpt

In this case, a slight accommodation takes place, but it is not sufficient to see clearly at a required object distance that is preferably at $A_{1N} = 2.5$ dpt. Here, the corrected spherical component of the spectacle lens requires an addition, which is given by the corrected near value $$M_N^{corr}(VD) = M_N(VD) - A_{1N} \quad (11a)$$

while the cylindrical component remains unchanged.

$$J_N^{corr}(VD) = J_N(VD) \quad (11b)$$

Thus, the corrected near power vector determined in step ST30b preferably reads:

$$P_N^{corr}(VD) = \begin{pmatrix} M_N^{corr}(VD) \\ J_N^{corr}(VD) \end{pmatrix} = P_N(VD) - \begin{pmatrix} A_{1N} \\ 0 \\ 0 \end{pmatrix} \quad (11)$$

c) $\Delta M \leq A_{1N}$

In this case, there is sufficient accommodation to meet any requirement on near vision without a spherical additional in the spectacle lens. Therefore, the corrected spherical component of the near vision is preferably equated with the distance measurement:

$$M_N^{corr}(VD) = M_F(VD) \quad (12a)$$

The cylindrical component of the measurement, however, corresponds to an accommodation of $-\Delta M$, although the portion of interest would only correspond to an accommodation of $-A_{1N}$. Therefore, the cylindrical component is preferably scaled back according to $$J_N^{corr}(VD) = J_F(VD) + \frac{A_{1N}}{\Delta M} \Delta J \quad (12b)$$

so that the corrected near power vector determined in step ST30c is preferably determined according to $$P_N^{corr}(VD) = \begin{pmatrix} M_N^{corr}(VD) \\ J_N^{corr}(VD) \end{pmatrix} = P_F(VD) + \frac{A_{1N}}{\Delta M} \begin{pmatrix} 0 \\ \Delta J \end{pmatrix} \quad (12)$$

Finally, the corrected near power vector is transformed back to corrected near refraction data $Sph_N^{corr}(VD), Cyl_N^{corr}(VD), Axis_N^{corr}(VD)$ in step ST32, preferably according to equation (3b). In step ST34, the corrected near refraction data $Sph_N^{corr}(VD), Cyl_N^{corr}(VD), Axis_N^{corr}(VD)$ is output as objective refraction values for near vision.

In a further aspect, which can preferably be used together with the above-described aspects or alone, first a very special sequence of method steps according to a preferred embodiment is described, the individual method steps being described in more detail in the following paragraphs. In this preferred embodiment, which is illustrated in FIG. 2, a method comprises the following steps in this order:

ST1A: determination of aberrometric data of the first eye for distance vision

ST1B: determination of aberrometric data of the first eye for near vision

ST2A: determination of aberrometric data of the second eye for distance vision

ST2B: determination of aberrometric data of the second eye for near vision

ST2C: determination of topographic data of the second eye

ST1C: determination of topographic data of the first eye

If only one eye is to be measured, the determination of the corresponding data of the second eye can be omitted. In this case, step ST1C can follow step ST1B immediately. This is illustrated by a dashed arrow in FIG. 2.

An interesting aspect is the collection of pupillometric data for at least two different conditions of the brightness captured by the respective eye. Here, it is particularly preferable to determine the pupillometric data together with the aberrometric or topographic data.

In a preferred embodiment, two different brightness target values are specified for the collection of the pupillometric data, said brightness target values particularly corresponding to two actually expected brightness values of an individual situation of wear. Thereby, preferably the measurement conditions under which the aberrometric data or topographic data is determined are selected such that the corresponding eye is subjected to one brightness according to the specified brightness target values.

However, this is not absolutely necessary. For example, in another preferred embodiment, the pupillometric data expected for the actual (individual) situation of wear can be derived from the pupillometric data collected under different measurement conditions. To this end, preferably the brightness during the pupillometric measurement is measured or known in advance. In a simplified example, the size (and position) of the pupil could be detected for two different measurement conditions "very bright" and "very dark", whereas the brightnesses actually expected under the situation of wear have deviating values "bright" and "dark". Thus, the size (and position) of the pupil for the situation of wear is calculated particularly by (e.g. linear or logarithmic) interpolation from the measured variables. Extrapolation can be used in an analogous way as well.

Preferably, the aberrometric data is determined under measurement conditions with low brightness. Thereby, a large pupil diameter is obtained, whereby in turn high measurement accuracy is achieved. Preferably, under the measurement conditions of the aberrometric measurement, i.e. at low brightness, the pupillometric measurement is performed for the low brightness. Particularly preferably, this is performed at the same time as the aberrometric measurement, or the two measurements are performed immediately one after the other, i.e. without changing the brightness in a way that could lead to a change in the pupil.

Preferably, the topographic data is determined under measurement conditions with high brightness (as secondary brightness). Preferably, a light pattern (e.g. in the form of Placido rings) is projected onto the cornea, the projections of which being detected at the cornea and evaluated for determining the topographic data. The use of measurements conditions with high brightness allows obtaining higher reliability and accuracy of the evaluation of the reflections and thus higher precision in the determination of the topographic data. Preferably, under the measurement conditions of the topographic measurement, i.e. at high brightness, the pupillometric measurement is performed for the high brightness (secondary pupillometric data). Particularly preferably, this is performed at the same time as the topographic measurement, or the two measurements are performed immediately on after the other, i.e. without changing the brightness in a way that could lead to a change in the pupil.

Since the brightness of the projected light pattern can be changed very easily, a preferred measurement system is preferably designed to adapt the brightness of the light pattern for the topographic measurement to the brightness desired for the pupillometric measurement. Preferably, the measurement system is designed to adapt an image-capturing device used for evaluating the reflections to the brightness desired for the pupillometric measurement.

Particularly preferably, the pupillometric data is collected from the same image data as the topographic data. Preferably, only one image (image data set) is created by means of a camera, said image being used for evaluating both the pupillometric data and the topographic data, which results in a particularly fast collection of the user data with little technical effort. However, this approach requires determining the pupil boundaries in an image in which the Placido are visible as well, for example. This can be accomplished by a suitable manual, semi-automatic, or automatic approach though. Here, in particular additional information, such as a color resolution of the camera, or a second camera for the pupillometric measurement with a (different) color filter (than the first camera used for the topographic measurement) can help distinguishing the relevant structures for the pupillometric measurement and the topographic measurement in the image or images. The pupillometric and topographic data can also be determined from a common, monochrome image if one takes geometric boundary conditions for the respective structures into account, for example.

It is not required (or desired) to collect topographic data in all cases. Even in a preferred apparatus, which particularly comprises a topography unit with a pattern projector and a topography evaluation device, the pupillometric data can also be collected for a high brightness value without any need to collect topographic data. In a preferred embodiment, the pattern projector of the topography unit is used to illuminate the at least one eye of the spectacle wearer up to a desired or suitably high brightness, which serves for collecting the pupillometric data at high brightness. In another preferred embodiment, in addition to or instead of the pattern projector, the apparatus comprises an illuminating device (e.g. one or more lamps) that provides for the required brightness for collecting the pupillometric data and is particularly controllable in terms of brightness in order to be able to adjust the brightness required according to an individual situation of wear.

If the apparatus comprises a topography unit, it is preferred that the apparatus cause shadowing of the eye from ambient light to obtain the best possible contrast of the projected pattern or the reflections also in the marginal regions of the cornea in the image data. Thereby, due to the shadowing of the eye, it is possible to perform a pupillometric measurement at low brightness also in a brightly illuminated space.

The size of the pupil depends not only on the illumination state, but also on the accommodative stimulation. Therefore, it is particularly preferred to adjust the accommodation stimulation device (i.e. the virtual target) to the individual situation of wear for which the pupillometric data is to be collected.

The integration of pupillometric measurements in aberrometric and topographic measurements for measurement conditions (in particular the brightness and/or the accommodation state) which correspond to the individual situation of wear, or the determination of information for conditions (in particular with respect to the brightness and/or accommodation state) which do not correspond to the measured conditions, can be performed by analogy with the approach described above for the brightness (in particular by interpolation or extrapolation).

While the term "distance vision" creates the impression as if the accommodation stimulation device describes a very remote but finite position or an infinitely remote position, it is preferred in practice that the eye be placed into a non-accommodated state ("fogged state") for "distance vision". This non-accommodated state of an eye is preferably obtained by (virtually) moving the virtual target beyond an infinitely remote position. That is, the optical system used for projecting the target (e.g. a diapositive) into the eye is set to a refractive power slightly larger than the refraction of the eye. Thereby, the test person cannot accommodate to the target anymore and the eye attains a relaxed, non-accommodated state.

To obtain reliable values in the determination of aberrometric data, it is preferred that the optical refractive power of the imaging unit of the accommodation stimulation device be larger than the refractive power of the eye as an optical system. Otherwise, the test person could achieve an accommodation to the target. The result of the aberrometric measurement could then rather reflect the refractive power of the imaging unit than the refractive power of the relaxed eye. Preferably, an approximated value of the refraction is determined by a pre-examination. This information is then used for virtual positioning of the target.

In the context of this invention, the term "distance vision" comprises in general for an accommodation stimulus either in the relaxed state ("fogged state") or for an infinite distance or a predetermined (large) distance (e.g. approximately 50 m).

Preferably, every step of determining aberrometric and/or pupillometric and/or topographic data can comprise a plurality of measurements under the same measurement conditions. This plurality of measurements is then preferably combined by a statistical evaluation to obtain a more precise and reliable result. For example, an average value of many measurements can be calculated, wherein irregularities in the measurements are neglected and/or implausible measurements are repeated. This does preferably hold true not only for distance vision measurements, but alternatively or in addition also for the pupillometric measurements and/or topographic measurements and/or the near vision measurements.

Preferably, the data for the near vision measurement have the analogous structure as the data for the distance vision measurement. Preferably, the only basic difference is the position of the virtual target. While for a typical distance vision measurement the target is moved to a virtual position beyond infinity, so that the eye cannot accommodate anymore, the target for the near vision measurement is moved to a virtual position closer to the eye of the test person. Preferably, the virtual position ($D_p$) of the target for near vision is calculated from the refractive power ($D_f$) for distance vision, which is determined in the distance vision measurement, and from the refractive power of the accommodation stimulus ($D_a$) according to the formula $D_p=D_f+D_a$, wherein the accommodation stimulus is usually negative (e.g. −2.5 dpt). To make sufficient accommodation for near vision easier for the test person, it is preferred to bring the target closer to the eye continuously and with not too high a speed.

For an individual near vision measurement, the target is preferably moved from an initial position (e.g. the distance vision position or another position preferably further remote than the near vision position) to the near vision position $D_p$ and only measurements at $D_p$ are performed. For more refined examinations, also several near vision measurements can be performed one after the other. For example, two near vision measurements can be performed: one at a first position $D_{p1}$ with $D_{a1}=-1.0$ dpt and another one at a second position $D_{p2}$ with $D_{a2}=-2.5$ dpt. To this end, the target is preferably moved from an initial position to the first position $D_{p1}$, where the first near vision measurement is performed. Preferably without any further delay, the target is moved further to the second position $D_{p2}$, where the second near vision measurement is performed. The test person of course has to try to follow the accommodation stimulus the whole time.

Irrespective of the number of near vision measurements actually performed, it is crucial that the test person follow the virtual target by the accommodation of the eye in the best possible way. Otherwise, the eye could remain in a state that accommodates less or even is relaxed, which would falsify the measurement. The always sufficient accommodation is supported preferably by the target initially being presented at a virtual position to which the test person can easily accommodate. Subsequently, the virtual position of the target is changed continuously with not too high a speed.

Preferably, topographic data is collected together with the pupillometric data for the high brightness, since this is possible preferably without any additional expenditure of time. As explained, there is no need to collect topographic data if it is not intended to subject the eye to the required or desired brightness or if this additional information is not required. In this case, the correspondingly high sensitivity of the image-capturing device and/or the pattern projectors as well as a topographic evaluation unit could be dispensed with.

Even if a topographic measurement is performed, the accommodation stimulus is preferably adapted to the requirements of the pupillometric measurement, as the accommodation state of the eye leaves the topography of the cornea substantially unaffected or as this influence is preferably neglected. Measurements are performed for different accommodation states and/or different brightnesses preferably also for the pupillometric measurements in the bright state, just like for the aberrometric measurements. As explained above, the topographic data is preferably used for optimizing the refraction and/or the lens based on complex eye models.

The selected order of measurements has substantial advantages over other approaches. For example, by performing the measurements at higher brightness after the measurements at lower brightness, the accuracy particularly of the aberrometric measurements and preferably also of the pupillometric measurements is improved without considerably increasing the overall expenditure of time for the data collection. This can be explained by the fact that the pupil needs some time to get used to a low brightness, while the decrease in pupil for an adaptation to a higher brightness can take place much faster.

If measurements are to be performed for both eyes, the pupillometric data for the brighter illumination state of both eyes (and in particular also the topographic measurements) is performed preferably only after the aberrometric measurements of both eyes. Thus, a negative influence on the measurement accuracy due to mutual influencing of the two eyes is reduced. Specifically, it has been found that the negative influence on the measurement accuracy due to mutual accommodative influencing of the two eyes is far less than a negative influence on the measurement accuracy due to mutual adaptive influencing by the brightness.

Moreover, it has been found that the measurement accuracy, in particular aberrometric measurements, is improved up to a certain extent as the test person or the eye gets used to the target and its virtual movement. It is therefore preferred that first of all both or all aberrometric measurements of said one eye be performed before the other eye is measured. Moreover, the effort involved in a new adjustment of the apparatus to the eye upon a change of the eye is reduced considerably. For this reason, for the pupillometric measurement in the bright state or for the topographic measurement, the measurement order of the two eyes is preferably interchanged. Thus, no change of eye and thus no new adjustment is required directly after the last aberrometric measurement.

In a preferred embodiment, the method of collecting a set of individual user data for the adaptation and optimization of a spectacle lens preferably comprises the following steps 1 to 9 in this order:

1. Start with the first eye, comprising:
   apparatus is adjusted to the first eye
   test person captures the target with the first eye
2. Aberrometric measurement of the first eye for distance vision (first aberrometric data of the first eye), comprising:
   pre-measurement for determining the required virtual distance of the target for stimulating the non-accommodated state ("fogged state")
   pupillometric measurement of the first eye for the darker state for distance vision (first primary pupillometric data of the first eye)
3. Aberrometric measurement of the first eye for near vision (in particular based on the results of the preceding step of determining the virtual position $D_a$ of the target for near vision) (second aberrometric data of the first eye), comprising:
   pupillometric measurement of the first eye for the darker state for near vision (second primary pupillometric data of the first eye)
4. First change of eye, comprising:
   apparatus is adjusted to the second eye
   test person captures the target with the second eye
5. Aberrometric measurement of the first eye for distance vision (first aberrometric data of the second eye), comprising:
   pre-measurement for determining the required virtual distance of the target for stimulating the non-accommodated state ("fogged state")
   pupillometric measurement of the second eye for the darker state for distance vision (first primary pupillometric data of the second eye)
6. Aberrometric measurement of the second eye for near vision (in particular based on the results of the preceding step of determining the virtual position $D_a$ of the target for near vision) (second aberrometric data of the second eye), comprising:
   pupillometric measurement of the second eye for the darker state for near vision (second primary pupillometric data of the second eye)
7. Topographic and pupillometric measurement of the second eye for the brighter state (topographic data and secondary pupillometric data of the second eye)
8. Second change of eye, comprising:
   apparatus is adjusted to the first eye
   test person captures the target with the first eye
9. Topographic and pupillometric measurement of the first eye for the brighter state (topographic data and secondary pupillometric data of the first eye)

If only one eye is to be measured, all steps for the second eye are preferably omitted.

LIST OF REFERENCE NUMERALS

ST10 collecting first measurement data
ST12 collecting a series of second measurement data
ST14 selecting second measurement data
ST16 detecting a photopic pupil radius
ST18 scaling the Zernike coefficients
ST20 determining propagated refraction values
ST22 outputting distance refraction values
ST24 transformation to power vectors ST26 determining the difference power vector ST28 checking the spherical component of the difference power vector ST30a, ST30b, ST30c determining a corrected power vector ST32 transforming the corrected power vector to refraction data ST34 outputting corrected near refraction data ST1A aberrometric measurement of the first eye for distance vision ST1B aberrometric measurement of the first eye for near vision ST1C aberrometric measurement of the second eye for distance vision ST2A aberrometric measurement of the second eye for near vision ST2B topographic measurement of the second eye ST2C topographic measurement of the first eye

The invention claimed is:

1. A method for objective refraction determination for an eye of a spectacle wearer, comprising:

collecting measurement data for the eye of the spectacle wearer, which data specifies at least a first set of Zernike coefficients $c_{2,F}^{0}$, $c_{2,F}^{2}$ and $c_{2,F}^{-2}$ for describing a wavefront aberration for a distance accommodation of the eye and a pupil radius $r_0$ of a situation of wear, as well as a second set of Zernike coefficients $c_{2,N}^{0}$, $c_{2,N}^{2}$ and $c_{2,N}^{-2}$ for describing a wavefront aberration for a near accommodation of the eye and the pupil radius $r_0$ of a situation of wear;

determining objective refraction data for sphere $Sph_N^{corr}$, cylinder $Cyl_N^{corr}$, and cylinder axis $Axis_N^{corr}$ of the eye for near vision such that the objective refraction data, in dependence on the first and second set of Zernike coefficients, satisfies the equations $$Sph_N^{corr} = M_N^{corr} + \sqrt{(J_{N,0}^{corr})^2 + (J_{N,45}^{corr})^2}$$

$$Cyl_N^{corr} = -2\sqrt{(J_{N,0}^{corr})^2 + (J_{N,45}^{corr})^2}$$

$$Axis_N^{corr} = \frac{1}{2}\arctan(-J_{N,0}^{corr}, -J_{N,45}^{corr}) + \frac{\pi}{2}$$

for a corrected power vector $$P_N^{corr} = \begin{pmatrix} M_N^{corr} \\ J_{N,0}^{corr} \\ J_{N,45}^{corr} \end{pmatrix}$$

for near vision, wherein the corrected power vector $P_N^{corr}$, in dependence on a difference $$\Delta P = \begin{pmatrix} \Delta M \\ \Delta J \end{pmatrix} = P_N - P_F$$

between a first power vector $$P_F = \begin{pmatrix} M_F \\ J_F \end{pmatrix} = \begin{pmatrix} -\frac{4\sqrt{3}}{r_0^2}c_{2,F}^{0} \\ -\frac{2\sqrt{6}}{r_0^2}c_{2,F}^{2} \\ -\frac{2\sqrt{6}}{r_0^2}c_{2,F}^{-2} \end{pmatrix}$$

and a second power vector $$P_N = \begin{pmatrix} M_N \\ J_N \end{pmatrix} = \begin{pmatrix} -\frac{4\sqrt{3}}{r_0^2}c_{2,N}^{0} \\ -\frac{2\sqrt{6}}{r_0^2}c_{2,N}^{2} \\ -\frac{2\sqrt{6}}{r_0^2}c_{2,N}^{-2} \end{pmatrix}$$

corresponds to the value $$P_N - \begin{pmatrix} A_{1N} \\ 0 \\ 0 \end{pmatrix},$$

if $\Delta M > A_{1N}$; and $$P_F + \frac{A_{1N}}{\Delta M}\begin{pmatrix} 0 \\ \Delta J \end{pmatrix},$$

corresponds to the value if $\Delta M \leq A_{1N}$
wherein $$A_{1N} = -\frac{1}{d}$$

is the spherical equivalent of a predetermined object distance d for near vision, and wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}$$

2. The method according to claim 1, wherein the collecting measurement data for the eye of the spectacle wearer comprises:

collecting first measurement data for the eye of the spectacle wearer for distance vision, which specifies the first set of Zernike coefficients;

collecting a series of second measurement data for the eye of the spectacle wearer for near vision for at least partly different accommodation of the eye; and selecting from the series the measurement data for which the strongest accommodation of the eye occurs as second measurement data, which specifies the second set of Zernike coefficients.

3. The method according to claim 2, wherein the collecting the first and/or or second measurement data comprises measuring refraction data of the eye by means of an autorefractor and/or by means of an aberrometer.

4. The method according to claim 1, wherein the collecting measurement data for the eye of the spectacle wearer comprises:
   collecting first measurement data for the eye of the spectacle wearer for distance vision, which specifies a first pupil radius $R_F$ and a first set of Zernike coefficients for describing a wavefront aberration measured for the first pupil radius $R_F$ and the distance accommodation of the eye;
   collecting second measurement data for the eye of the spectacle wearer for near vision, which specifies a second pupil radius $R_N$ and a second set of Zernike coefficients for describing a wavefront aberration measured for the second pupil radius $R_N$ and a near accommodation; and
   detecting the pupil radius $r_0$ of the situation of wear,
   wherein the first and second sets of Zernike coefficients for describing the wavefront aberrations for the pupil radius $r_0$ of the situation of wear are specified by scaling of the first and second sets of Zernike coefficients, respectively, for describing the measured wavefront aberrations depending on the relationship $$\lambda_i = \frac{r_0}{R_i}$$

of the pupil radius $r_0$ to the first (i=F) and second (i=N) pupil radius $R_i$, respectively.

5. The method according to claim 4, wherein the first and second sets of Zernike coefficients for describing the measured wavefront aberrations, which are comprised by the first and second measurement data, respectively, comprise at least Zernike coefficients up to the fourth order, and wherein the first and second sets of Zernike coefficients for describing the wavefront aberrations for the photopic pupil radius $r_0$ depend on the first (i=F) and second (i=N) sets of Zernike coefficients, respectively, of the measured wavefront aberrations according to $$c_{2,i}^0(r_0) = \lambda_i^2(c_{2,i}^0(R_i) + \sqrt{15}(\lambda_i^2-1)c_{4,i}^0(R_i))$$

$$c_{2,i}^2(r_0) = \lambda_i^2(c_2^2(R_i) + \sqrt{15}(\lambda_i^2-1)c_{4,i}^2(R_i))$$

$$c_{2,i}^{-2}(r_0) = \lambda_i^2(c_2^{-2}(R_i) + \sqrt{15}(\lambda_i^2-1)c_{4,i}^{-2}(R_i)).$$

6. The method according to claim 4, wherein the first and second sets of Zernike coefficients for describing the measured wavefront aberrations, which are comprised by the first and second measurement data, respectively, comprise at least Zernike coefficients up to the sixth order, and wherein the first and second sets of Zernike coefficients for describing the wavefront aberrations for the photopic pupil radius $r_0$ depend on the first (i=F) and second (i=N) sets of Zernike coefficients, respectively, of the measured wavefront aberrations according to $$c_{2,i}^0(r_0) = \lambda_i^2(c_{2,i}^0(R_i) + \sqrt{15}(\lambda_i^2-1)c_{4,i}^0(R_i) + \sqrt{21}(\lambda_i^2-1)(3\lambda_i^2-2)c_{6,i}^0(R_i))$$

$$c_{2,i}^2(r_0) = \lambda_i^2(c_{2,i}^2(R_i) + \sqrt{15}(\lambda_i^2-1)c_{4,i}^2(R_i) + \sqrt{21}(\lambda_i^2-1)(3\lambda_i^2-2)c_{6,i}^2(R_i))$$

$$c_{2,i}^{-2}(r_0) = \lambda_i^2(c_{2,i}^{-2}(R_i) + \sqrt{15}(\lambda_i^2-1)c_{4,i}^{-2}(R_i) + \sqrt{21}(\lambda_i^2-1)(3\lambda_i^2-2)c_{6,i}^{-2}(R_i)).$$

7. The method according claim 4, wherein the collecting measurement data for the eye of the spectacle wearer comprises:
   collecting the first measurement data at a first measurement position; and
   collecting the second measurement data at a second measurement position;
   wherein determining objective refraction data of the eye for near vision comprises:
   determining the first power vector $$P_F(VD_F) = \begin{pmatrix} M_F(VD_F) \\ J_F(VD_F) \end{pmatrix}$$

from the first set of Zernike coefficients, comprised by the first measurement data or scaled according to claim 4, depending on a distance $VD_F$ of an evaluation position from the first measurement position such that $M_F(VD_F)$ describes the spherical equivalent and $J_F(VD_F)$ describes the cylindrical portion of the wavefront aberration at the evaluation position for the distance accommodation of the eye; and
   determining the second power vector $$P_N(VD_N) = \begin{pmatrix} M_N(VD_N) \\ J_N(VD_N) \end{pmatrix}$$

from the second set of Zernike coefficients, comprised by the second measurement data or scaled according to claim 4, depending on the distance $VD_N$ of the evaluation position from the second measurement position such that $M_N(VD_N)$ describes the spherical equivalent and $J_N(VD_N)$ describes the cylindrical portion of the wavefront aberration at the evaluation position for the near accommodation of the eye.

8. The method according to claim 7, wherein the first power vector and/or the second power vector is determined such that it satisfies the equation $$P_i(VD_i) = \begin{pmatrix} Sph_i(VD_i) + \dfrac{Cyl_i(VD_i)}{2} \\ -\dfrac{Cyl_i(VD_i)}{2}\cos 2Axis_i(VD_i) \\ -\dfrac{Cyl_i^2(VD_i)}{2}\sin 2Axis_i(VD_i) \end{pmatrix}$$

with $$Sph_i(VD_i) = \frac{Sph_i(0)}{1 + VD_i \times Sph_i(0)}$$

$$Cyl_i(VD_i) = \frac{Sph_i(0) + Cyl_i(0)}{1 + VD_i \times (Sph_i(0) + Cyl_i(0))} - \frac{Sph_i(0)}{1 + VD_i \times Sph_i(0)}$$

$$Axis_i(VD_i) = Axis_i(0)$$

and $$Sph_i(0) = -\frac{4\sqrt{3}}{r_0^2}c_{2,i}^0 + \frac{2\sqrt{6}}{r_0^2}\sqrt{(c_{2,i}^{-2})^2 + (c_{2,i}^2)^2}$$

$$Cyl_i(0) = -\frac{4\sqrt{6}}{r_0^2}\sqrt{(c_{2,i}^{-2})^2 + (c_{2,i}^2)^2}$$

$$Axis_i(0) = \frac{1}{2}\arctan(c_{2,i}^2, c_{2,i}^{-2}) + \frac{\pi}{2}$$

for i=F, N, wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}$$

and wherein $c_{2,i}^0$, $c_{2,i}^2$, and $c_{2,i}^{-2}$ designate the second-order Zernike coefficients for distance vision (i=F) and near vision (i=N), which are comprised by the first (i=F) and second (i=N) measurement data, respectively, or scaled according to claim 4.

9. An apparatus for collecting a set of individual user data for adapting and optimizing spectacles, the apparatus comprising:
- an aberrometer device adapted to collect aberrometric data of at least one eye of the spectacle wearer at least for a first accommodation state of the eye for a first primary brightness;
- an illuminating device adapted to generate a secondary brightness greater than the first primary brightness; and
- a pupillometer device adapted to collect first primary pupillometric data of the at least one eye for the first primary brightness and to collect secondary pupillometric data of the at least one eye for the secondary brightness,
- wherein the apparatus is adapted to perform a method according to claim 1.

10. The apparatus according to claim 9, wherein the aberrometer device is further adapted to collect aberrometric data of at least one eye for a second accommodation state of the eye for a second primary brightness, the value of which being below that of the secondary brightness.

11. The apparatus according to claim 10, wherein the pupillometer device is further adapted to collect second primary pupillometric data of the at least one eye for the second primary brightness.

12. The apparatus according to claim 9, wherein the aberrometer device comprises an accommodation stimulation device adapted to project a virtual target into the at least one eye and to change the virtual position of the virtual target between a position for stimulating a distance accommodation and a position for stimulating a near accommodation.

13. The apparatus according to claim 9, further comprising:
- a pattern projector adapted to project a light pattern onto the at least one eye; and
- a topography evaluation device adapted to determine topographic data from reflections of the light pattern at the eye.

14. A computer program product comprising computer-readable instructions, which, when loaded in a memory of a computer and executed on the computer, cause the computer to perform a method according to claim 1.

15. An apparatus for objective refraction determination for an eye of a spectacle wearer, comprising:
- a measurement data collecting interface for collecting measurement data for the eye of the spectacle wearer, which specifies at least a first set of Zernike coefficients $c_{2,F}^0$, $c_{2,F}^2$, and $c_{2,F}^{-2}$ for describing a wavefront aberration for a distance accommodation and a photopic pupil radius $r_0$ of the eye, and a second set of Zernike coefficients $c_{2,N}^0$, $c_{2,N}^2$, and $c_{2,N}^{-2}$ for describing a wavefront aberration for a near accommodation and the photopic pupil radius $r_0$ of the eye; and
- a refraction data determining device for determining objective refraction data for sphere ($Sph_N^{corr}$), cylinder ($Cyl_N^{corr}$), and cylinder axis ($Axis_N^{corr}$) of the eye for near vision such that the objective refraction data, in dependence on the first and second sets of Zernike coefficients, satisfies the equations $$Sph_N^{corr} = M_N^{corr} + \sqrt{(J_{N,0}^{corr})^2 + (J_{N,45}^{corr})^2}$$

$$Cyl_N^{corr} = -2\sqrt{(J_{N,0}^{corr})^2 + (J_{N,45}^{corr})^2}$$

$$Axis_N^{corr} = \frac{1}{2}\arctan(-J_{N,0}^{corr}, -J_{N,45}^{corr}) + \frac{\pi}{2}$$

for a corrected power vector $$P_N^{corr} = \begin{pmatrix} M_N^{corr} \\ J_{N,0}^{corr} \\ J_{N,45}^{corr} \end{pmatrix}$$

for near vision, wherein the corrected power vector $P_N^{corr}$, in dependence on a difference $$\Delta P = \begin{pmatrix} \Delta M \\ \Delta J \end{pmatrix} = P_N - P_F$$

between a first power vector $$P_F = \begin{pmatrix} M_F \\ J_F \end{pmatrix} = \begin{pmatrix} -\frac{4\sqrt{3}}{r_0^2} c_{2,F}^0 \\ -\frac{2\sqrt{6}}{r_0^2} c_{2,F}^2 \\ -\frac{2\sqrt{6}}{r_0^2} c_{2,F}^{-2} \end{pmatrix}$$

and a second power vector $$P_N = \begin{pmatrix} M_N \\ J_N \end{pmatrix} = \begin{pmatrix} -\frac{4\sqrt{3}}{r_0^2} c_{2,N}^0 \\ -\frac{2\sqrt{6}}{r_0^2} c_{2,N}^2 \\ -\frac{2\sqrt{6}}{r_0^2} c_{2,N}^{-2} \end{pmatrix}$$

corresponds to the value $$P_N - \begin{pmatrix} A_{1N} \\ 0 \\ 0 \end{pmatrix},$$

if $\Delta M > A_{1N}$; and
corresponds to the value $$P_F + \frac{A_{1N}}{\Delta M}\begin{pmatrix} 0 \\ \Delta J \end{pmatrix},$$

if $\Delta M \leq A_{1N}$,
wherein $$A_{1N} = -\frac{1}{d}$$

is the spherical equivalent of a predetermined object distance d for near vision, and wherein $$\arctan(x, y) := \begin{cases} \arctan(y/x), & x > 0 \\ \arctan(y/x) + \pi, & x < 0, y > 0 \\ \arctan(y/x) - \pi, & x < 0, y < 0 \\ \pi/2, & x = 0, y > 0 \\ -\pi/2, & x = 0, y < 0 \end{cases}.$$

16. A method for collecting a set of individual user data of a spectacle wearer for the adaptation and optimization of spectacles, comprising the following steps in this order:
collecting first aberrometric data of a first eye of the spectacle wearer for a first accommodation state of the first eye for a first primary brightness (ST1A), wherein together with collecting first aberrometric data, first primary pupillometric data for the first eye is collected; and
collecting secondary pupillometric data for the first eye of the spectacle wearer for a secondary brightness, the value of which being above that of the first primary brightness (ST1C).

17. The method according to claim 16, which prior to the step of collecting secondary pupillometric data further comprises:
collecting second aberrometric data of the first eye of the spectacle wearer for a second accommodation state of the first eye for a second primary brightness, the value of which being below that of the secondary brightness (ST1B).

18. The method according to claim 17, further comprising, together with collecting second aberrometric data, collecting second primary pupillometric data for the first eye.

19. The method according to claim 17, which after the step of collecting first aberrometric data of the first eye, and prior to the step of collecting secondary pupillometric data of the first eye, further comprises the following steps in this order:
collecting first aberrometric data of a second eye of the spectacle wearer for a first accommodation data of the second eye for the first primary brightness (ST2A), wherein together with collecting first aberrometric data of the second eye, first primary pupillometric data for the second eye is collected; and
collecting secondary pupillometric data of the second eye of the spectacle wearer for the secondary brightness (ST2C).

20. The method according to claim 19, which prior to the step of collecting secondary pupillometric data of the second eye further comprises:
collecting second aberrometric data of the second eye of the spectacle wearer for a second accommodation data of the second eye for the second primary brightness (ST2B).

21. The method according to claim 20, further comprising, together with collecting second aberrometric data of the second eye, collecting second primary pupillometric data for the second eye.

22. The method according to claim 17, further comprising:
collecting third aberrometric data of the first and/or second eye(s) of the spectacle wearer for a third accommodation state of the first or second eye for a third primary brightness; and
collecting third primary pupillometric data for the first or second eye together with collecting third aberrometric data of the first or second eye.

23. The method according to claim 19, wherein the first accommodation specifies a distance accommodation of a non-accommodated state, and wherein the second accommodation state specifies a near accommodation.

24. The method according to claim 17,
wherein the accommodation states are stimulated by projecting a virtual target into the respective eye; and
further comprising, between collecting the first and second aberrometric data of the first and/or second eye(s), continuously approximating a virtual position of the virtual target to the first or second eye.

25. The method according to claim 16, further comprising, together with collecting the secondary pupillometric data of the first or second eye, collecting topographic data of the first or second eye for the secondary brightness.

26. The method according to claim 25, wherein the collecting topographic data comprises projecting a light pattern onto the eye and collecting image data of the eye from which both the light reflections, generated by the projected light pattern, for evaluating the topographic data and the secondary pupillometric data is determined.

* * * * *